United States Patent
Gofman et al.

(10) Patent No.: US 10,320,212 B2
(45) Date of Patent: *Jun. 11, 2019

(54) RAPID CHARGING AND POWER MANAGEMENT OF A BATTERY-POWERED FLUID ANALYTE METER

(71) Applicant: Ascensia Diabetes Care Holdings AG, Basel (CH)

(72) Inventors: Igor Gofman, Croton-on-Hudson, NY (US); Jun Chen, Warren, NJ (US)

(73) Assignee: ASCENSIA DIABETES CARE HOLDINGS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/047,769

(22) Filed: Jul. 27, 2018

(65) Prior Publication Data

US 2018/0358828 A1    Dec. 13, 2018

Related U.S. Application Data

(63) Continuation of application No. 15/496,623, filed on Apr. 25, 2017, now Pat. No. 10,050,458, which is a
(Continued)

(51) Int. Cl.
  *G08B 21/00* (2006.01)
  *H02J 7/00* (2006.01)
  (Continued)

(52) U.S. Cl.
  CPC ........ *H02J 7/0047* (2013.01); *A61B 5/14532* (2013.01); *G01N 33/48785* (2013.01);
  (Continued)

(58) Field of Classification Search
  CPC ........ H02J 7/0047; H02J 7/007; H02J 7/0073; H02J 7/0078; H02J 7/0091;
  (Continued)

(56) References Cited

U.S. PATENT DOCUMENTS 3,599,071 A    8/1971    Lapuyade
3,852,652 A    12/1974   Jasinski
(Continued)

FOREIGN PATENT DOCUMENTS

CN    1319274    10/2001
CN    1330427    1/2002
(Continued)

OTHER PUBLICATIONS

Isidor Buchmann, *The Battery Fuel Gauge*, http://www.batteryuniversity.com/partone-18.htm (Jul. 2003) (3 pages).
(Continued)

*Primary Examiner* — Anh V La
(74) *Attorney, Agent, or Firm* — Nixon Peabody LLP

(57) ABSTRACT

A system and method is described for rapid charging and power management of a battery for a meter. A charger component is operably associated with the meter and is capable of executing a rapid charge algorithm for a rechargeable battery. The algorithm includes monitoring for a connection to an external power source and implementing a charging routine of a battery at a first charge rate and then at a second charge rate. The second charge rate is lower than the first charge rate. A temperature rise in the rechargeable battery due to the first charge rate has a negligible heat transfer effect on the fluid sample. The meter can also include a power switch for controlling current flow to a battery fuel gauge. The power switch is open when the meter enters into a sleep mode. The state of battery charge is determined after the meter exits the sleep mode.

16 Claims, 8 Drawing Sheets

Related U.S. Application Data continuation of application No. 15/058,711, filed on Mar. 2, 2016, now Pat. No. 9,667,078, which is a continuation of application No. 13/789,104, filed on Mar. 7, 2013, now Pat. No. 9,312,720, which is a continuation of application No. 13/436,416, filed on Mar. 30, 2012, now Pat. No. 8,441,363, which is a continuation of application No. 12/129,185, filed on May 29, 2008, now Pat. No. 8,164,468.

(60) Provisional application No. 61/012,690, filed on Dec. 10, 2007.

(51) Int. Cl.
  *G01R 31/3842* (2019.01)
  *A61B 5/145* (2006.01)
  *G01N 33/487* (2006.01)
  *G01R 31/36* (2019.01)

(52) U.S. Cl.
  CPC .......... *G01R 31/3842* (2019.01); *H02J 7/007* (2013.01); *H02J 7/0073* (2013.01); *H02J 7/0078* (2013.01); *H02J 7/0091* (2013.01); *A61B 2560/0214* (2013.01); *G01R 31/3646* (2019.01)

(58) Field of Classification Search
  CPC ........ A61B 5/14532; A61B 2560/0214; G01N 33/48785; G01R 31/3624; G01R 31/3682; G01R 31/3842; G01R 31/3646
  USPC ......... 340/636.2, 636.1, 603, 573.1; 600/365
  See application file for complete search history.

(56) References Cited

U.S. PATENT DOCUMENTS

| | | |
|---|---|---|
| 4,670,703 A | 6/1987 | Williams |
| 5,266,880 A | 11/1993 | Newland |
| 5,507,288 A | 4/1996 | Bocker |
| 5,686,808 A | 11/1997 | Lutz |
| 5,818,202 A | 10/1998 | Miyamoto |
| 5,883,497 A | 3/1999 | Turnbull |
| 6,489,749 B1 | 12/2002 | Nakashimo |
| 6,558,320 B1 | 5/2003 | Causey, III |
| 6,641,533 B2 | 11/2003 | Causey, III |
| 6,768,425 B2 | 7/2004 | Flaherty |
| 6,828,761 B1 | 12/2004 | Suzuki |
| 7,071,654 B2 | 7/2006 | Suzuki |
| 7,107,160 B2 | 9/2006 | Bean |
| 7,557,540 B2 | 7/2009 | Kao |
| 7,646,175 B2 | 1/2010 | Ikeda |
| 7,768,408 B2 | 8/2010 | Reggiardo |
| 8,164,468 B2 | 4/2012 | Gofman |
| 8,441,363 B2 | 5/2013 | Gofman |
| 8,770,482 B2 * | 7/2014 | Ackermann .............. G06F 8/65 235/439 |
| 9,312,720 B2 | 4/2016 | Gofman |
| 9,667,078 B2 | 5/2017 | Gofman |
| 2001/0045355 A1 | 11/2001 | Gephart |
| 2002/0002326 A1 | 1/2002 | Causey, III |
| 2002/0021108 A1 | 2/2002 | Suzuki |
| 2002/0170823 A1 | 11/2002 | Housefield |
| 2004/0124810 A1 | 7/2004 | Smallwood |
| 2006/0245131 A1 | 11/2006 | Ramey |
| 2007/0013345 A1 | 1/2007 | Ikeda |
| 2007/0156033 A1 | 7/2007 | Causey, III |
| 2007/0279011 A1* | 12/2007 | Jones ...................... H01G 9/14 320/167 |
| 2008/0048614 A1 | 2/2008 | Partin |
| 2008/0139910 A1* | 6/2008 | Mastrototaro ...... G06F 19/3456 600/365 |
| 2008/0212249 A1 | 9/2008 | Grewe |
| 2009/0121685 A1 | 5/2009 | Eto |
| 2009/0318834 A1 | 12/2009 | Fujiwara |

FOREIGN PATENT DOCUMENTS

| | | |
|---|---|---|
| CN | 1441510 | 9/2003 |
| CN | 1732607 A | 2/2006 |
| CN | 1255676 C | 5/2006 |
| CN | 101008667 | 8/2007 |
| JP | H 07-177672 | 7/1995 |
| JP | H 08-098426 | 4/1996 |
| JP | H 11-097074 | 4/1999 |
| JP | 2002-010503 | 1/2002 |
| JP | 2002-191136 | 7/2002 |
| JP | 2003-520091 | 7/2003 |
| JP | 2003-526108 | 9/2003 |
| JP | 2004-198196 | 7/2004 |
| JP | 2006-074935 | 3/2006 |
| JP | 2006-339140 | 12/2006 |
| JP | 2007-20245 | 1/2007 |
| JP | 2007-28745 | 2/2007 |
| KR | 100163476 | 12/1998 |
| WO | WO 2004/055536 | 7/2004 |
| WO | WO 2006/020212 | 2/2006 |
| WO | WO 2006/135838 | 12/2006 |
| WO | WO 2007/108515 | 9/2007 |
| WO | WO 2007/122787 A1 | 11/2007 |

OTHER PUBLICATIONS

International Search Report for PCT/US2008/006789 dated Nov. 25, 2008 (6 pages).

Partial International Search Report for International Application No. PCT/US2008/006789 dated Sep. 30, 2008 (2 pages).

Extended European Search Report for Application No. 18165631.5, dated Sep. 3, 2018 (7 pages).

* cited by examiner

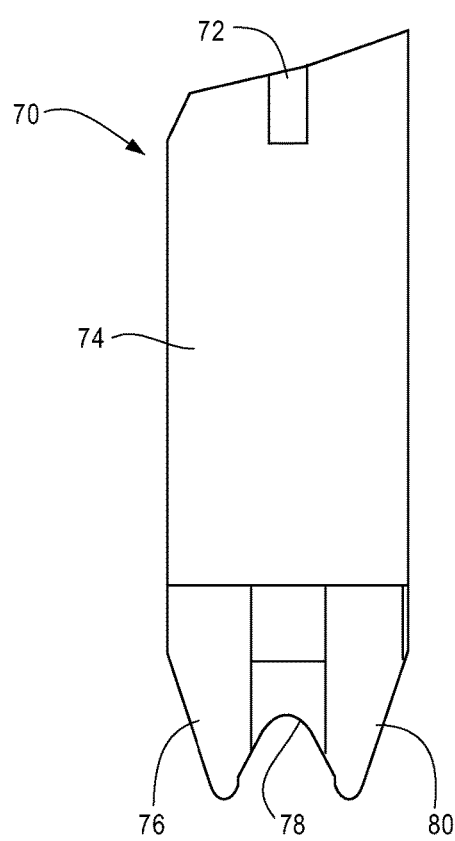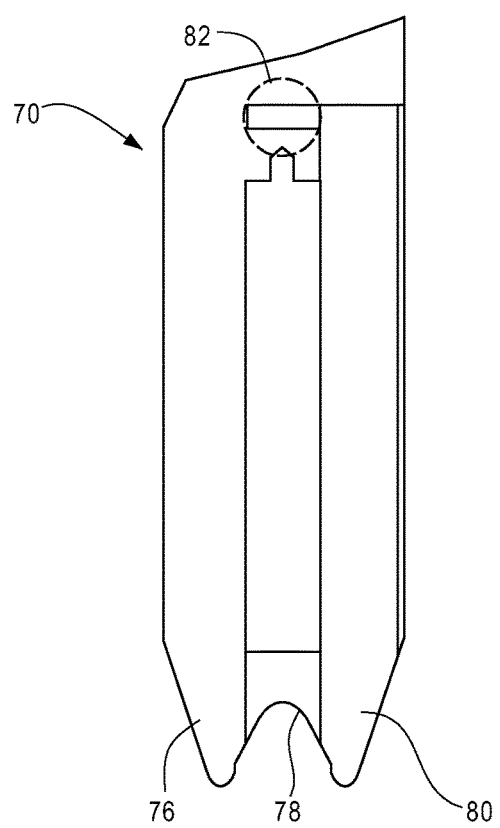

RAPID CHARGING AND POWER MANAGEMENT OF A BATTERY-POWERED FLUID ANALYTE METER

CROSS REFERENCE TO RELATED APPLICATIONS

This application is a continuation of U.S. patent application Ser. No. 15/496,623, filed Apr. 25, 2017, now allowed, which is a continuation of U.S. patent application Ser. No. 15/058,711, filed Mar. 2, 2016, now U.S. Pat. No. 9,667,078, which is a continuation of U.S. patent application Ser. No. 13/789,104, filed Mar. 7, 2013, now U.S. Pat. No. 9,312,720, which is a continuation of U.S. patent application Ser. No. 13/436,416, filed Mar. 30, 2012, now U.S. Pat. No. 8,441,363, which is a continuation of U.S. patent application Ser. No. 12/129,185, filed May 29, 2008, now U.S. Pat. No. 8,164,468, which claims priority to and the of U.S. Patent Application No. 61/012,690, filed Dec. 10, 2007, each of which are hereby incorporated by reference herein in their entireties.

FIELD OF THE INVENTION

The present invention generally relates to test sensors powered by a rechargeable battery, and more particularly, to rapid charging and power management of a battery-powered sensor.

BACKGROUND OF THE INVENTION

The quantitative determination of analytes in body fluids is of great importance in the diagnoses and maintenance of certain physical conditions. For example, lactate, cholesterol, and bilirubin should be monitored in certain individuals. In particular, determining glucose in body fluids is important to individuals with diabetes who must frequently check the glucose level in their body fluids to regulate the glucose intake in their diets. The results of such tests can be used to determine what, if any, insulin or other medication needs to be administered. In one type of testing system, test sensors are used to test a fluid such as a sample of blood.

Many individuals test their blood glucose several times per day. Thus, the individuals often must carry with them a meter for determining the glucose concentration of their blood. The individuals may also carry with them other analyte-testing instruments, including test sensors, a lancet, disposable lancets, a syringe, insulin, oral medication, tissues, or the like. Thus, the individuals are able to perform testing of their blood glucose at different locations including their homes, places of employment (e.g., office buildings or work sites), places of recreation, or the like. Carrying the meter and/or other analyte-testing instruments to these various locations may be inconvenient.

Blood glucose meters can be powered using various types of powering configurations such as batteries or adapters that can be plugged into a standard outlet. The use of batteries allows the device to be portable and mobile without using a power outlet. Batteries available for use in blood glucose meters include both disposal batteries and rechargeable batteries. The use of a rechargeable battery for a blood glucose meter requires the battery to have a charge for the meter to function. Sometimes when a battery is discharged, a critical situation may arise that requires an emergency blood glucose test.

Measurement of blood glucose concentration is typically based on a chemical reaction between blood glucose and a reagent. The chemical reaction and the resulting blood glucose reading as determined by a blood glucose meter is temperature sensitive. Therefore, a temperature sensor is typically placed inside a blood glucose meter. The calculation for blood glucose concentration in such meters typically assumes that the temperature of the reagent is the same as the temperature reading from the sensor placed inside the meter. However, if the actual temperature of the reagent and the meter are different, the calculated blood glucose concentration will not be accurate. An increase in temperature or the presence of a heat source within a blood glucose meter will generally result in an erroneous measurement of blood glucose.

Power management in a battery-powered blood glucose meter can include using a battery fuel gauge to monitor the state of battery charge. A battery fuel gauge typically monitors, on a continual basis, the current flowing in both directions through the battery of the meter. However, such continuous monitoring also requires the battery fuel gauge to operate constantly, which results in increased power consumption, even when the battery-powered blood glucose meter is in a sleep mode. The increased power consumption requires a larger battery size and increases battery cost, particularly for portable devices.

It would be desirable to have a battery-powered meter that can be rapid charged without a significant temperature rise. It would also be desirable to manage the power consumption of a battery-powered meter to minimize power consumption during periods of non-use while maintaining an accurate assessment of the state of battery charge.

SUMMARY OF THE INVENTION

According to one embodiment, a battery-powered meter is adapted to determine an analyte concentration of a fluid sample using a test sensor. The meter includes a port sized to receive at least a portion of a test sensor. A front portion comprises a display operable to display the analyte concentration of the fluid sample. A user-interaction mechanism is operable to control the meter. The meter also includes a housing for a rechargeable battery. A battery charger component is operably associated with the meter. The battery charger component is capable of executing a rapid charge algorithm for a rechargeable battery. The algorithm comprises monitoring for a connection to an external power source. If the external power source is detected, a charging routine is implemented for the rapid charging of a battery at a first charge rate until a first predetermined event occurs followed by charging the battery at a second charge rate until a second predetermined event occurs. The second charge rate is lower than the first charge rate.

According to another embodiment, a method of rapid charging a battery in a fluid analyte meter includes monitoring for a connection to an external power source. A rapid charge routine is implemented for charging the battery at a first charge current rate over a first predetermined time period. Following the first predetermined time period, a normal charge routine is implemented for charging the battery at a second charge current rate over a second predetermined time period. The first charge current rate is greater than the second charge current rate. The first predetermined time period is at least partially based on an approximated temperature rise in the battery due to a charge current associated with the first charge current rate.

According to a further embodiment, a computer-readable medium is encoded with instructions for directing a rapid charge of a battery for a meter operable to determine an analyte concentration of a fluid sample. The instructions include monitoring for a connection to an external power source and implementing a rapid charge routine for charging the battery at a first charge current until a first predetermined event occurs. Following the occurrence of the first predetermined event, a normal charge routine is implemented for charging the battery at a second charge current until a second predetermined event occurs. The first charge current is greater than the second charge current. The temperature rise is monitored for at least one of the battery and the meter, with the monitoring occurring at one or more predetermined time intervals. If the temperature rise in the battery or the meter exceed a predetermined threshold value, the rapid charge routine or the normal charge routine are canceled.

According to another embodiment, a portable meter having a circuit is configured with a battery to provide power to a sensing element within the circuit. The meter includes a processor powered by the circuit. The processor is configured to operate the meter in an active mode and a sleep mode. A fuel gauge is powered by the circuit. The fuel gauge is configured to track state of battery charge data received from the battery during active mode operation of the meter. An interface is configured to transfer state of battery charge data from the fuel gauge to the processor. A power switch controls current flow to the fuel gauge and is configured to be open and closed by the processor. The processor signals the power switch into an open position if the meter enters into the sleep mode and the processor signals the power switch into a closed position if the meter enters into an active mode. Prior to entering the sleep mode, the processor is configured to record a first state of battery charge for the battery and a first time reference immediately prior to the meter entering said sleep mode. The processor is further configured to determine a second state of battery charge at a second reference time immediately after the meter exits from the sleep mode into the active mode. The second state of battery charge is determined based on the recorded first state of charge, the first reference time, the second reference time, and a predetermined energy usage rate of the meter during the sleep mode.

According to another embodiment, a method of power management includes a battery-powered meter that is configured to operate in an active mode and a standby mode. The batter-powered meter includes a battery fuel gauge and a microcontroller. The method includes the steps of receiving a first request to enter into the standby mode. A first state of charge is recorded for a battery of the meter. The recording occurs at a first reference time immediately after the first request is received. The first reference time is recorded using the microcontroller. The meter is entered into the standby mode with the power to the battery fuel gauge being switched off in the standby mode. A second request to exit the standby mode and enter the active mode is received at a second reference time. The second reference time occurs after the first reference time. In response to the second request, a second reference time is immediately recorded and the microcontroller determines a second state of battery charge based on the first reference time, the second reference time, a standby mode current, and a standby mode voltage of the meter.

According to a further embodiment, a computer-readable memory medium has stored thereon instructions for managing the power of a battery-powered meter operating in an active mode and a sleep mode. The instructions includes the steps of receiving a first request to enter into the sleep mode and recording a first state of charge for a battery of the meter. The recording occurs at a first reference time immediately after the first request is received. A first reference time is recorded. The meter is entered into the standby mode wherein power to a battery fuel gauge is switched off in the standby mode. A second request is received at a second reference time to exit the sleep mode and enter the active mode. The second reference time occurs after the first reference time. Immediately after the second request, a second reference time is recorded. A second state of battery charge is determined based on the first reference time, the second reference time, a sleep mode current, and a sleep mode voltage.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1a illustrates a sensor including a lid according to one embodiment.

FIG. 1b illustrates the sensor of FIG. 1a without the lid.

FIG. 2b illustrates a side view of the meter from FIG. 2a.

Figure 2A:
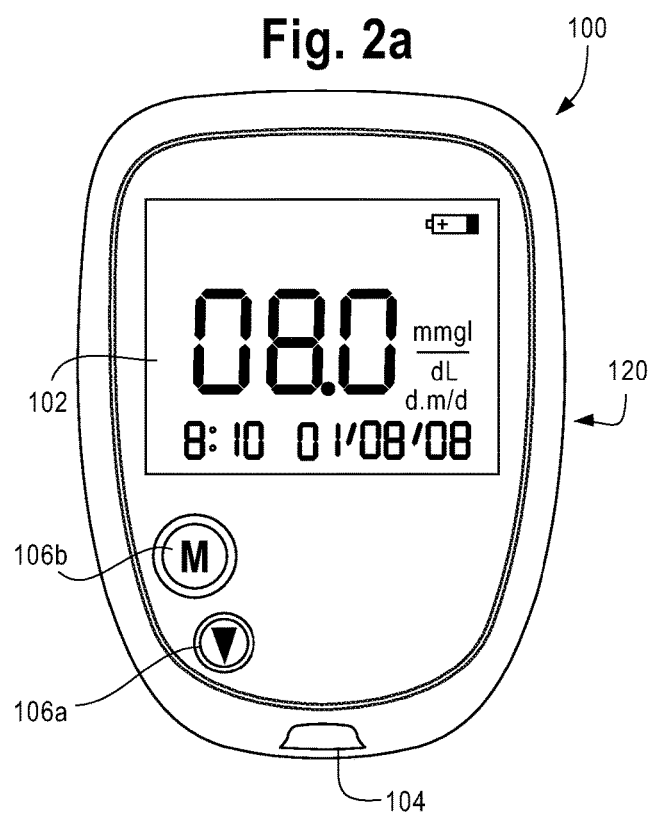
FIG. 2a illustrates a front view of a meter with a display according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

A system and method for rapid charging of a battery for a meter is disclosed herein. When the rechargeable battery for a battery-powered meter becomes discharged, a critical situation arises for a user in the event that an emergency test is needed, such as, for example, when using a blood glucose meter. Such a critical situation can be minimized for meters powered with rechargeable batteries. A discharged battery can be charged for a very short period of time using a rapid charge technique to provide enough of a charge to energize the meter to complete one or more tests, such as analyzing blood glucose concentration, while minimizing temperature rise in the meter.

FIGS. 1a-b and FIGS. 2a-b illustrates certain embodiments of meters, such as blood glucose meters, according to the present disclosure. The devices can contain electrochemical test-sensors that are used to determine concentrations of at least one analyte in a fluid. Analytes that may be determined using the device include glucose, lipid profiles (e.g., cholesterol, triglycerides, LDL and HDL), microalbumin, hemoglobin $A_1C$, fructose, lactate, or bilirubin. The present invention is not limited, however, to devices for determining these specific analytes and it is contemplated that other analyte concentrations may be determined. The analytes may be in, for example, a whole blood sample, a blood serum sample, a blood plasma sample, or other body fluids like ISF (interstitial fluid) and urine.

Although the meters of FIGS. 1 and 2 are shown as being generally rectangular, it should be noted that the cross section of the meters used herein may be other shapes such as circular, square, hexagonal, octagonal, other polygonal shapes, or oval. A meter is typically made of a polymeric material. Non-limiting examples of polymeric materials that may be used in forming the meter include polycarbonate, ABS, nylon, polypropylene, or combinations thereof. It is contemplated that the meter may be made using non-polymeric materials.

According to certain embodiments, the test-sensors for the devices are typically provided with a capillary channel that extends from the front or testing end of the sensors to biosensing or reagent material disposed in the sensor. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that an electrical signal indicative of the analyte (e.g., glucose) concentration in the fluid being tested is supplied and subsequently transmitted to an electrical assembly.

Reagent materials that may be used to determine the glucose concentration include glucose oxidase. It is contemplated that other reagent material may be used to determine the glucose concentration such as glucose dehydrogenase. If an analyte other than glucose is being tested, different reagent material will likely be used.

One example of a test-sensor is shown in FIGS. 1a, 1b. FIGS. 1a, 1b depict a test-sensor 70 that includes a capillary channel 72, a lid 74, and a plurality of electrodes 76, 78, and 80. FIG. 1b is illustrated without a lid. The plurality of electrodes includes a counter electrode 76, a detection electrode 78, and a working (measuring) electrode 80. As shown in FIG. 1b, the test-sensor 70 includes a fluid-receiving area 82 that contains reagent. It is contemplated that other electrochemical test-sensors may be employed.

Figure 2B:
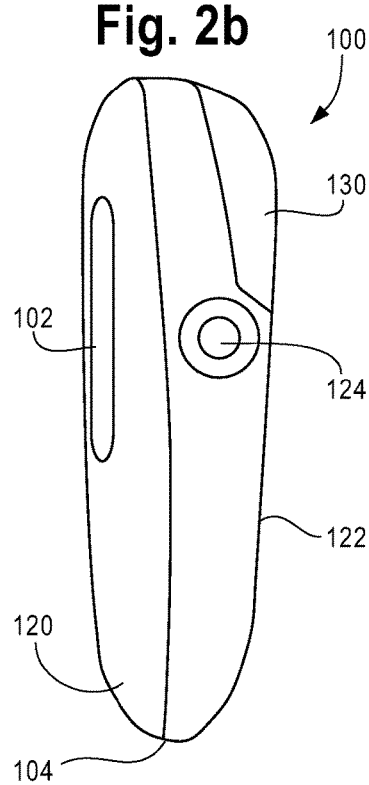

Referring to FIGS. 2a-b, one example of a meter 100 is illustrated according to an embodiment of the present disclosure. The meter 100 is desirably sized so that it may fit generally within a user's purse or pocket. Thus, it is desirable, though not necessary, that the meter 100 have a long-dimension of less than approximately 2 to 3 inches to enhance portability. It is also desirable that the meter 100 have a footprint area of less than about 6 to 9 $in^2$. The meter 100 may even have a footprint area in the range of about 3 $in^2$.

As shown in FIGS. 2a and 2b, the meter 100 includes a display 102 visible through a front portion 120, a test-sensor dispensing port 104, and a user interface mechanism 106. The user interface mechanism 106 may be buttons, scroll wheels, etc. FIG. 2a shows the meter 100 with a number of display segments. After a user places a fluid (e.g., blood) on a test-sensor, the analyte (e.g., glucose) level is determined by the meter 100, which displays the reading on the display 102.

The meter 100 typically includes a microprocessor or the like for processing and/or storing data generated during the testing procedure. For example, the user-interface mechanism 106a-b may be depressed to activate the electronics of the meter 100, to recall and view results of prior testing procedures, to input meal and/or exercise indicators, or the like. The meter 100 may also use the same or a different microprocessor for power management, including executing routines to control recharging functions of the meter 100 for battery-powered devices.

The test sensor dispensing port 104 is adapted to receive and/or hold a test sensor and assist in determining the analyte concentration of a fluid sample. To communicate at least the analyte concentration to the user, the meter 100 includes a display 102. One example of a display 102 that may be used in the meter 100 is a liquid-crystal display. The liquid-crystal display typically shows information from the testing procedure and/or in response to signals input by the user-interface mechanism 106a-b. Other types of displays can include, for example, light emitting diode (LED), organic light emitting diode (OLED), liquid-crystal display (LCD) with backlight, thin film transistor (TFT), a segmented display or other types of transmissive displays. The type of display can have minimal or significant effects on the amount of energy used by a meter.

The meter 100 may be powered by a main power supply, a battery, or any other suitable power source. The main power supply may include internally operated AC and/or DC power supplies. It can be desirable that the meter 100 be powered by battery due to the portable nature of the meter 100. A battery housing 130 may be located in a back portion 122 of a meter 100 or within the front portion 120.

In certain embodiments, the battery for the meter 100 is rechargeable via a main power source that can be connected to the meter 100 through a power adapter receptacle 124. Different types of rechargeable battery configurations may be used to power the meter 100 including, for example, lithium ion (Li-Ion), lithium polymer (Li—Po), nickel cadmium (NiCd) or nickel metal hydride (NiMH).

For certain meter 100 configurations, a rechargeable battery (not shown) is removed from the battery housing 130 of the meter 100 and placed into a separate charger that is, for example, plugged into a standard AC wall outlet or connected to a car battery. Other meters can be charged by plugging one end of a special adapter into the power adapter receptacle 124 of the meter 100 while the battery remains in the battery housing 130. A second end of the special adapter is then plugged into the AC power outlet to charge the battery. In certain embodiments, the meter 100 may be powered by connecting one end of the special adapter to a source on a computer, such as a Universal Serial Bus (USB) port, and the second end to the power adapter receptacle 124.

Battery chargers are capable of providing a fast or rapid charge to a rechargeable battery by using a higher charging current than would be typically used to charge the battery, with minimal degradation of the battery. This principal of rapid charge of a battery also applies to battery charger integrated circuits. For example, rechargeable batteries, such as Li-Ion, LiPo, NiCd and NiMH, allow a fast charging rate of up to approximately 2 C to 5 C without a significant reduction in battery life. The term C is defined as the rated capacity of the given battery that is being charged. For example, a battery with a 200 mAh capacity has a 1 C rate of 200 mA, a 2 C rate of 400 mA and a 5 C rate of 1,000 mA.

In certain embodiments, a very short charge time for a battery at a high charging rate can provide sufficient energy to a meter battery to allow for several fluid analyte concentration tests.

In certain embodiments, a device may issue an early warning alert that, for example, approximately ten fluid analyte concentration tests can be completed with the remaining charge in the battery. The device may further issue a final alert indicating that, for example, two or fewer test can be completed based on the remaining charge. In such situations, it would be beneficial to charge the battery at a high charging rate for a very short charge time, particularly after the final alert.

An example demonstrating the amount of energy used in a single analyte concentration test is provided for meters similar to the embodiments described herein. Assuming the test takes up to two minutes and that the display 102 for the meter 100 is running continuously during this time, the meter 100 having a transmissive display (e.g., OLED, LCD with backlight, TFT) can consume approximately up to 40 milliamperes (mA) from the rechargeable battery at 3.6 volts (V). The equation below mathematically shows the relationship of the energy consumed by the meter relative to the duration of the test, the battery voltage, and the current:

$$E_{FROM\ BATTERY} = I \times V_{BAT} \times t_{OPERATION}$$

where: $E_{FROM\ BATTERY}$ is the energy consumption
$V_{BAT}$ is the voltage of the battery
I is the current drawn by the meter
$t_{OPERATION}$ is the duration of the analyte concentration test Applying the values from the example above:

$$E_{FROM\ BATTERY} = 40 \times 10^{-3}\ A \times 3.6V \times 2\ min \times 60\ sec \approx 17J$$

Another example demonstrates a rapid charge scenario for a rechargeable battery for a meter similar to the embodiments described herein. The meter can be plugged into a power source using a special adapter that may be connected to a USB port or into another power source. In this example, an internal battery charging circuit provides a charging rate of 2 C. After the battery has been charged, for example, for certain period of time, $t_{charging}$ (e.g., 30 seconds, one minute), the energy received from the battery charger is approximated by the following relationship:

$$E = I_{CHARGING} \times V_{BAT} \times t_{CHARGING}$$

where: $E_{CHARGED}$ is the energy received from the battery charger
$V_{BAT}$ is the voltage of the battery
$I_{CHARGING}$ is the charging current (e.g., for 200 mAh battery $I_{CHARGING}$=400 mA at a charge rate of 2 C)
$t_{charging}$ is the charge duration (e.g., one minute in our example)

Applying the values from the example above:

$$E_{CHARGED} = 0.4\ A \times 3.6V \times 60\ sec = 86.4\ J$$

This example demonstrates that after charging the battery for approximately 60 seconds at a 2 C current rate, enough energy can be provided to a rechargeable battery to perform approximately five tests (86.4 J/17 J≈5) based on the single test energy draw example demonstrated above, for which the energy consumption of one test was calculated to be 17 Joules.

The use of rapid charging for a meter battery can lead to an increase in the temperature of the meter and change the resulting analyte concentration reading that is output by the meter. Therefore, while rapid charging is desirable for temperature sensitive meters, such as, for example, meters having rechargeable batteries, it is further desirable to minimize temperature rise for the device.

The embodiments described herein allow for the rapid charging of the battery for a meter performing temperature-sensitive tests, such as portable meters, using a power source for rapid charging the battery for a short period of time. In certain embodiments, the charging process continues at a normal charge rate after the rapid charging is completed. The embodiments desirably minimize the temperature rise of the meter.

In certain embodiments, the internal charging circuit for the meter may have a rapid charge mode and a normal charge mode. An internal charging circuit can further limit the temperature rise of the meter by reducing the charging rate from a rapid charge rate to a normal charge rate that has a negligible temperature rise. Such an embodiment can be particularly beneficial when a user does not unplug the special adapter from the power source following a rapid charge.

In certain embodiments, once a meter battery is connected to an external power source, such as a USB port or a power adapter, the internal charging circuit or battery charger can first go into a rapid charge mode, and subsequently switch to a normal or reduced charge mode according to the temperature rise criteria for the particular portable temperature-sensitive meter. For example, the rapid charge mode can have a charging rate up to approximately 5 C. In other embodiments, the charging rate may exceed 5 C. The charge rate will vary on such criteria as the configuration of the battery or the current output of the power source (e.g., USB port or power adapter). In the example of a lithium ion battery, the maximum charging rate is approximately 2 C. In the example of a USB port, the current capability may be either 100 mA or 500 mA.

In certain embodiments, when the rapid charge of the rechargeable battery is complete, an internal electronic circuit can provide a perceivable signal to the user, such as an audio or light signal. The signal will let the user know that the battery has sufficient energy to power the desired test(s). At this point, the user will have the option of unplugging the meter from the power source and performing the analyte concentration test. If the user does not unplug the meter from the power source, the charging circuit for the meter can be configured to switch into a normal charge mode that provides, for example, a charging rate in the range of approximately 0.5 C to 1 C. In the normal charge mode, less heat is generated to the battery than with the higher charging rate of the rapid charge mode. In certain embodiments, the normal charge mode can be set to a charge current level that allows an equilibrium between heat dissipation due to charging and heat irradiation from the temperature-sensitive meter to the surrounding atmosphere (e.g., air). In certain embodiments, it is desirable to maintain the temperature in the normal charge mode that was achieved during the rapid charge mode.

Figure 3:
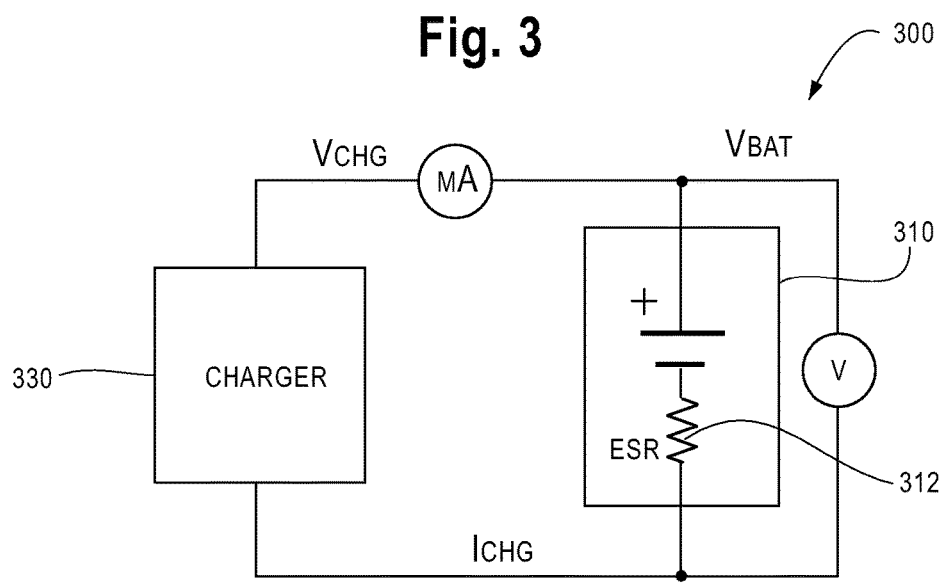
FIG. 3 illustrates a charging circuit for a rechargeable battery according to one embodiment.

Referring now to FIG. 3, a schematic of a charging circuit 300 for a rechargeable battery 310 is illustrated according to certain embodiments. The charging circuit 300 experiences a battery temperature rise during the charging of the battery 310, similar to what be experienced during the charging of a meter battery. The battery 310 has an internal equivalent series resistance (ESR) 312 that causes the heat dissipation of the battery. Furthermore, a temperature rise in the battery 310 will be proportional to the charge time and to the second order of the charge current. ESR varies according to the type of battery. For example, a lithium polymer battery that is 50 percent discharged has a typical equivalent series resistance of approximately less than 0.07 Ohms. The charging circuit 300 further includes a charger 330, such as an external power source, connected to the battery 310.

Another example demonstrates an approximation of the amount of heat generated in a battery in a rapid charge mode. Assuming a lithium ion battery, such as the one discussed above having a current rate of 2 C and a capacity of 200 mAh, the value for the charging current is calculated as follows:

$$I_{CHG}=2\times 200=400 \text{ mA}=0.4 \text{ A}$$

The power dissipation, or heat caused by the internal equivalent series resistance 312 of battery 310 during the charging process, can be calculated using the following relationship:

$$P=I_{CHG}^2 \times \text{ESR}$$

Applying the values from above, the battery power dissipation is:

$$P_{DISP}=(0.4 \text{ A})^2 \times 0.07 = 0.012 \text{ W}$$

The energy dissipation for an assumed 60 second rapid charge is calculated to be 0.72 Joules using the following relationship:

$$Q=P_{DISP}\times t=0.012 \text{ W}\times 60 \text{ sec}=0.72 \text{J}$$

The general relationship for the heat transferred is express as:

$$Q=m\times (\Delta T)\times C_P(\text{J})$$

where Q=heat transferred;
ΔT=the change in temperature;
Cp=the specific heat of the battery; and
m=mass.

The specific heat will vary depending on the type of rechargeable battery that is used. The specific heat, in the example of a lithium polymer battery made from mixed plastic/foil/fiber materials, is within 1 to 3 J/gram ° C. To be conservative in calculating temperature rise, the lower value of the specific heat will be used. The mass for a typical 200 mAh lithium polymer battery is about 5 grams. Applying the above values and results, the heat transfer relationship yields a temperature rise of:

$$\Delta T = \frac{Q(\text{J})}{m\times C_P} = \frac{0.72 \text{ J}}{5\times 1} = 0.14° \text{ C.}$$

In the above example, which is applicable to rapid charging scenarios that can occur in certain embodiments, a temperature rise of 0.14° C. or less can be considered to be negligible and would not be expected to affect an analyte concentration reading. In other embodiments, a temperature rise of approximately 1° C. or less may be considered negligible for analyte concentration testing of a fluid sample. Furthermore, the above example conservatively estimates a higher temperature rise than would be expected since the heat transfer between the meter and air was not subtracted from the calculated result nor was the temperature rise calculated based on the entire battery-meter system. Rather the temperature rise calculation was conservatively estimated for the battery only.

The above calculation is based on a series of calculations using an assumed 60 second rapid charge time along with other assumed factors. As the calculations demonstrate, a shorter rapid-charge time of, for example, thirty seconds at a 2 C charge rate provides enough energy for more than one test of an analyte concentration for the assumed meter.

Figure 4:
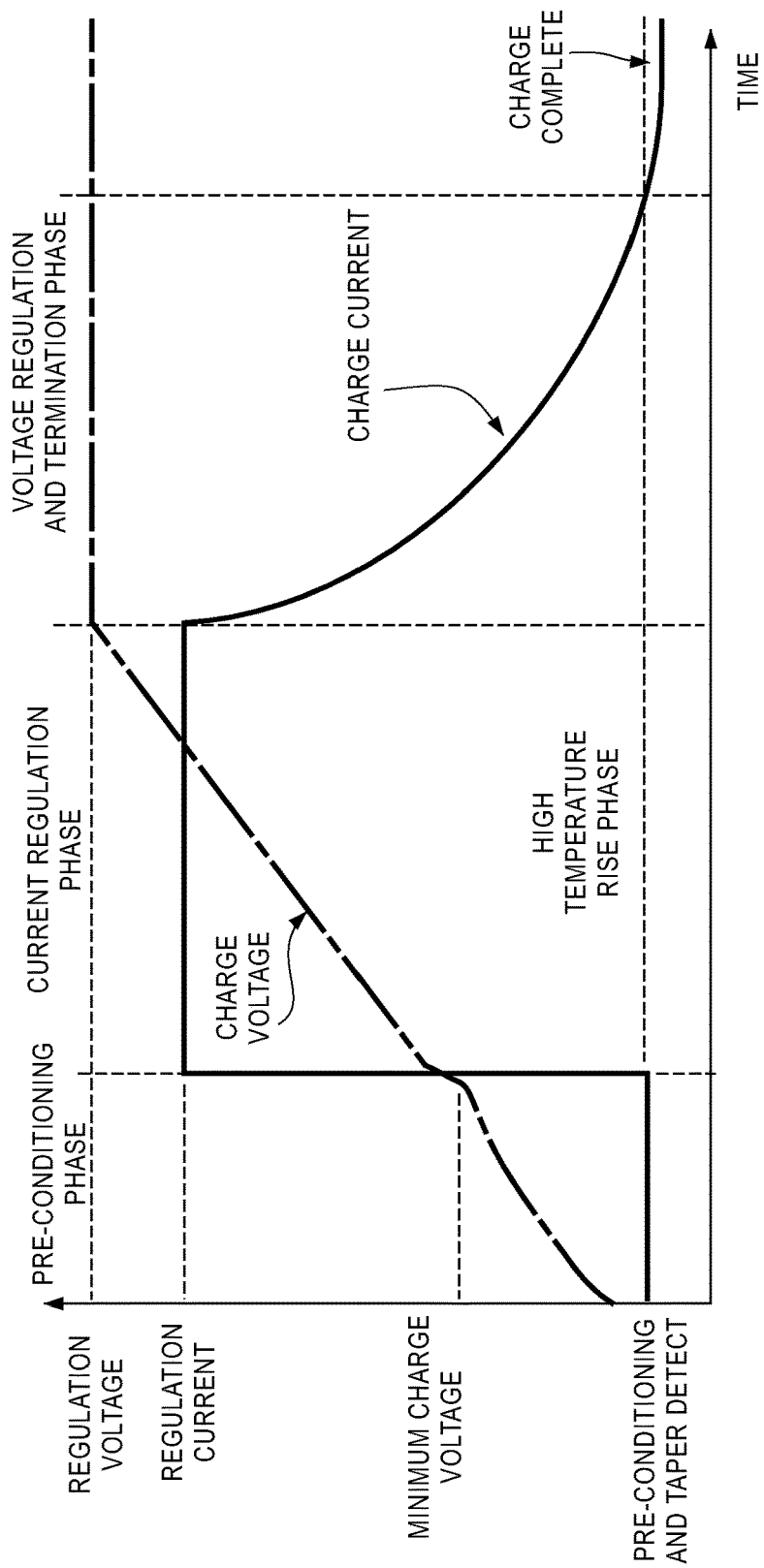
FIG. 4 illustrates a charging algorithm having a high temperature-rise phase used to charge a battery.
Figure 5:
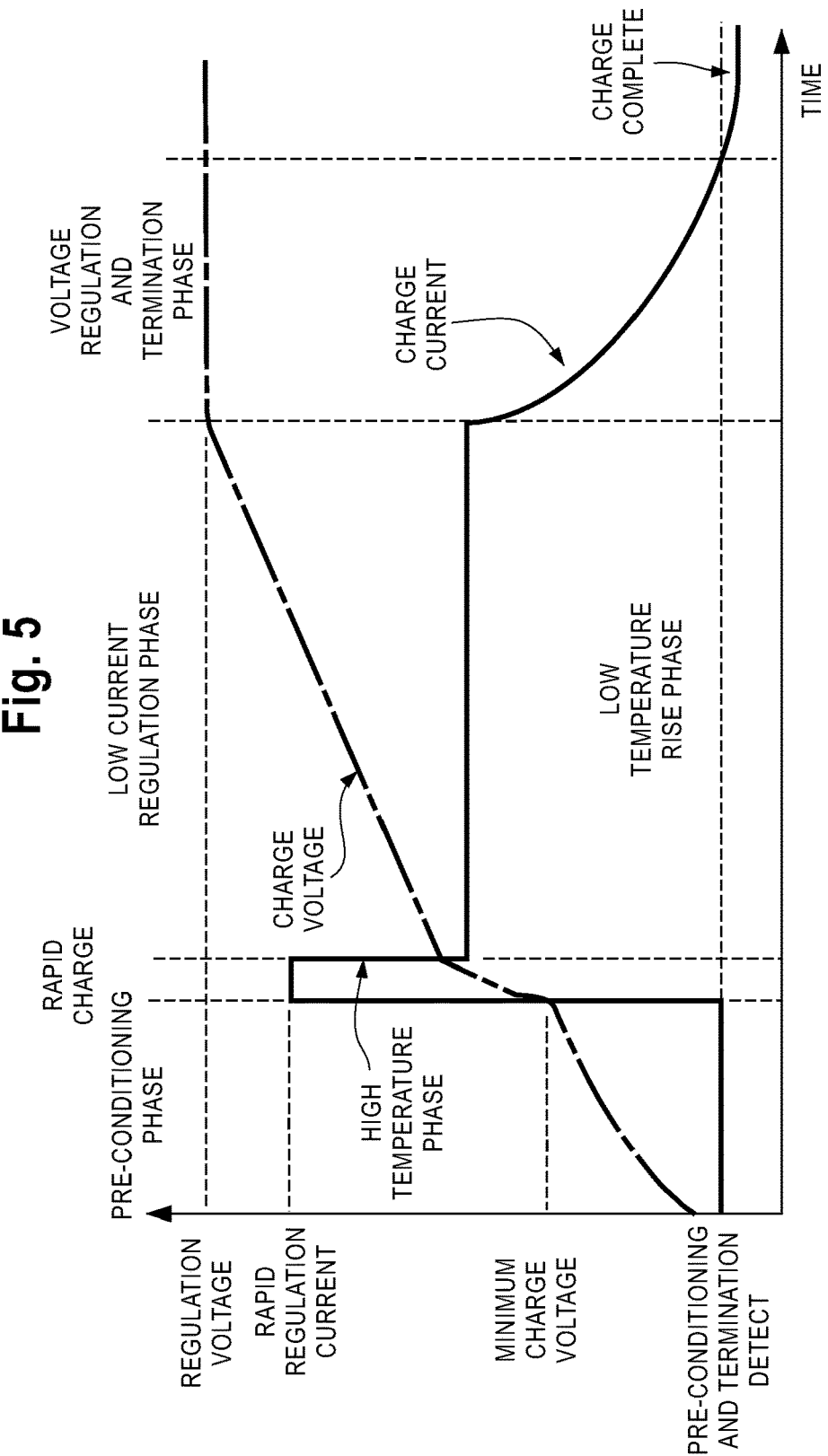
FIG. 5 illustrates a current regulation phase having a high and low temperature-rise phase according to one embodiment.

Referring now to FIGS. 4 and 5, a standard charging algorithm is illustrated in FIG. 4 and embodiments of a rapid charge algorithm are disclosed in FIG. 5. The charging sequences for the algorithms of FIGS. 4 and 5 begin with a pre-conditioning phase, then progress to a current regulation phase, and close with voltage regulation and termination phases, after which charging of the battery is considered complete. The rapid charge algorithm of FIG. 5 further breaks up the current regulation phase into two separate steps. The current regulation phase starts out in a rapid charge mode or high current regulation phase having a high temperature rise and after the lapse of a predetermined period of time or after a predetermined charge voltage is achieved, the charge current will decrease or move into a low current regulation having a low temperature rise.

For both FIGS. 4 and 5, as long as the battery is receiving energy from the battery charger, the battery can continue charging until the battery reaches a regulation voltage at which point the charge current decreases until the charge is considered complete. The difference between FIGS. 4 and 5 is that the current charge remains constant in the standard charging algorithm (FIG. 4) from the time the minimum charge voltage is reached up until the time the regulation voltage is reached. However, in the rapid charge algorithm the charge current rises for a short period after the minimum charge voltage is reached and then the charge voltage drops, so that the temperature rise is minimized to a point of being negligible to any temperature sensitive tests that may be conducted with the meter. The charge time for the algorithm of FIG. 5 can be longer than the standard charging algorithm illustrated in FIG. 4.

Figure 6:
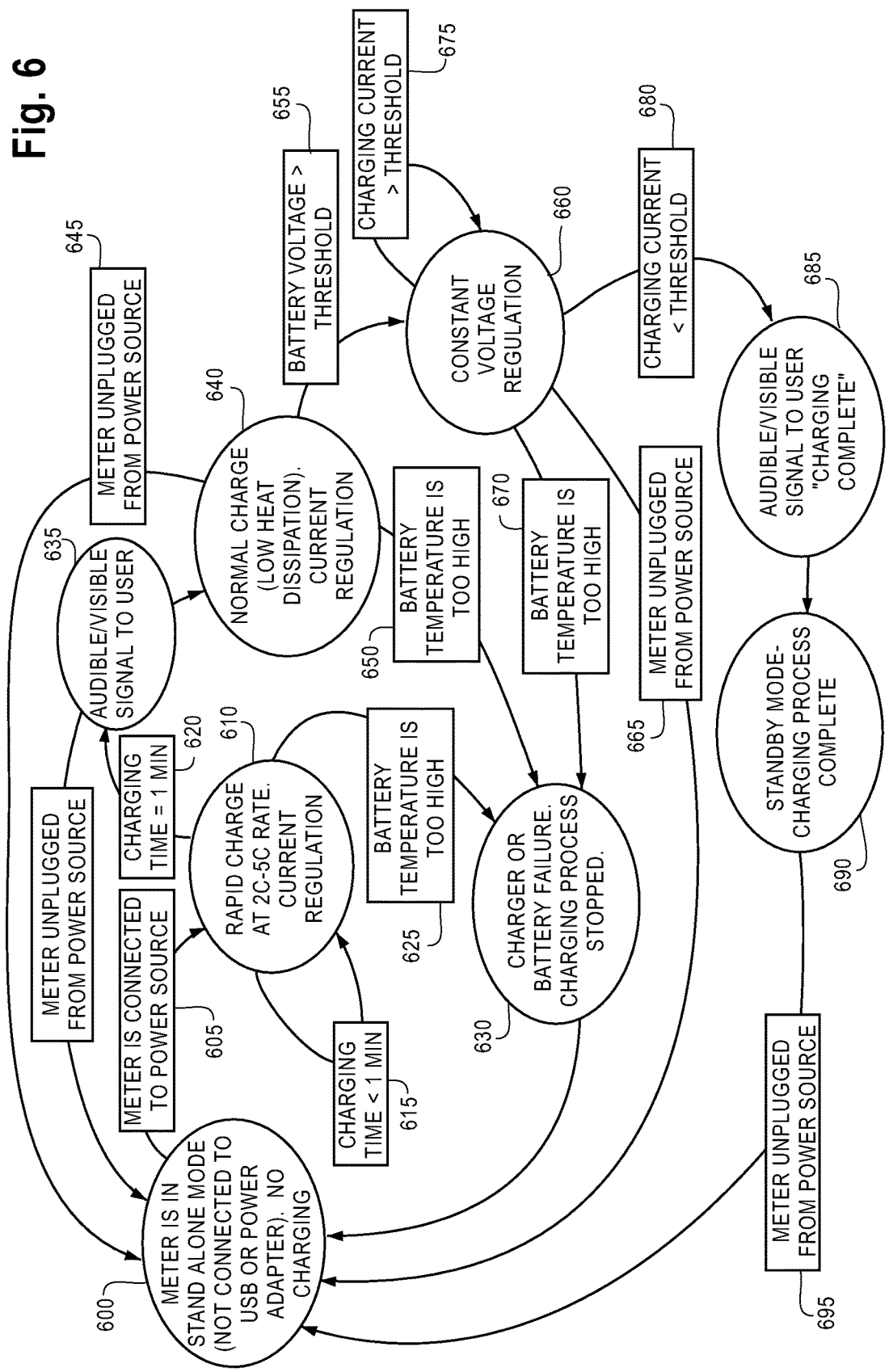
FIG. 6 illustrates a finite state machine of a method to rapid-charge a rechargeable battery that minimizes temperature rise according to one embodiment.

Referring now to FIG. 6, an embodiment of a finite state machine is illustrated for rapid charging of a meter battery. The embodiment of FIG. 6 can be implemented, for example, using a controller or microprocessor. The meter starts in a standalone mode or no charging mode at step 600 in which the meter is not connected to a power source such as, for example, a power adapter or USB port. The meter is connected to a power source at step 605, which in turn, can initiate a charging algorithm in a meter having a rechargeable battery. In certain embodiments, the battery begins charging at a rapid charge rate at step 610 in which the current is regulated at, for example, a charge current of 2 C to 5 C. The rapid charge rate continues for a predetermined period of time at step 615, such as, for example thirty seconds or one minute. The rapid charge period can also be determined based on the battery achieving a threshold charge voltage without exceeding, for example, a certain time period or temperature rise.

During the rapid charge stage 610, an assessment may be made whether the battery temperature is too high at step 625 through monitoring of a temperature sensor. In certain embodiments, if it is established that the battery temperature is too high at step 625, the charging process can be stopped and a determination made at step 630 whether a charger and/or battery failure has occurred. At this point, the meter can return to the stand alone mode at step 600 and corrective action can be taken. In certain embodiments, once the threshold time period or voltage is reached at step 620, an audible or visible alarm or other signal at step 635 can be used to alert the user that the rapid charge is complete.

The rapid charge method of the finite state machine can then enter a normal charge phase at step 640 in which the charge current is reduced. In certain embodiments, the meter may then be disconnected from the power source at step 645.

Another assessment can also be made at this stage of whether the battery temperature is too high at step 650, which may lead to the charging process being stopped and a determination made at step 630 whether a charger and/or battery failure has occurred. During the normal charge mode, a routine can also assess at step 655 whether the battery voltage exceeds a threshold value. If a threshold voltage is exceeded, the charging can enter a constant voltage regulation phase at step 660. In certain embodiments, the meter may be disconnected from the power source at step 665. A further assessment can also be made at this point of whether the battery temperature is too high at step 670, which again, may lead to the charging process being stopped and a determination made at step 630 whether a charger and/or battery failure has occurred. In certain embodiments, a routine can periodically check whether the charge current exceeds a certain threshold value at step 675. If the charge current exceeds the threshold value, the charging routine can continue in the constant voltage regulation phase at step 660. If the charging current is less than a predetermined threshold value at step 680, the user can be signaled at step 685 using, for example, an audible or visual cue that charging for the battery or system is complete. The meter can at this point enter into a standby mode at step 690 with the charging process completed. The user may at this point unplug the meter at step 695 from the power source at which point the meter returns to the stand alone mode at step 600.

The embodiments disclosed herein for the rapid charging of a battery for a temperature-sensitive meter provide a number of benefits. For example, instead of constantly charging a battery at high constant rate until the voltage reaches a predefined level, the battery is being charged at the high rate only for a short period of time to provide enough energy for a limited number of blood glucose concentration tests. After rapid charging, the charger may switch into low-rate or normal charging mode that maintains the battery temperature as it was at the end of rapid charging phase. The embodiments disclosed herein allow a user, in the example of a meter, to enjoy the benefits associated with using a meter operating on a rechargeable battery while further allowing the user to quickly recharge the meter without sacrificing test accuracy caused by temperature rise.

In certain embodiments, the temperature rise can be monitored at predetermined periodic intervals for the battery or the meter. If the temperature rise in the battery of the meter exceeds a predetermined threshold value, the rapid charge routine or the normal charge routine can be cancelled. Such a temperature rise may be indicative of a failure in the meter device or the battery.

In certain embodiments, a battery-powered meter is adapted to determine an analyte concentration of a fluid sample using a test sensor. The meter includes a test port or opening sized to receive at least a portion of the test sensor. A front portion has a display operable to display the analyte concentration of the fluid sample. A user-interaction mechanism can be used to control the meter. A housing can be provided for holding a rechargeable battery. A battery charger component can be operably associated with the meter and can further execute a rapid charge algorithm for a rechargeable battery. In one embodiment, the algorithm includes: (i) monitoring for a connection to an external power source, and (ii) if the external power source is detected, implementing a charging routine for the rapid charging of a battery at a first charge rate until a first predetermined event occurs followed by charging said battery at a second charge rate until a second predetermined event occurs. The second charge rate is lower than the first charge rate. In other embodiments, a temperature rise in the rechargeable battery due to the first charge rate has a negligible heat transfer effect on the fluid sample.

In other embodiments, the battery-powered meter is a blood glucose meter. The battery-powered meter can have a first charge rate ranging from 2 C to 5 C. The battery-powered meter can also have a second charge rate that is less than 1 C. The battery charger component can also be a part of an integrated circuit.

In other embodiments, the first predetermined event for the battery-powered meter is a lapsing of a predetermined time period. The predetermined time period can be approximately one minute or less. The first predetermined event for the battery-powered meter can also be exceeding a predetermined charge voltage or exceeding a threshold temperature in the rechargeable battery. The first predetermined event for the battery-powered meter can also be exceeding a threshold temperature in the meter.

In other embodiments, the external power source for the battery-powered meter can be a port on a computing device. The rechargeable battery can also be periodically monitored for elevated temperature readings.

In certain embodiments, a method of rapid charging a battery in a blood glucose or other fluid analyte meter includes monitoring for a connection to an external power source and implementing a rapid charge routine for charging the battery at a first charge current rate over a first predetermined time period. Following the first predetermined time period, the method further includes implementing a normal charge routine for charging the battery at a second charge current rate over a second predetermined time period. The first charge current rate is greater than the second charge current rate. The first predetermined time period is at least partially based on an approximated temperature rise in said battery due to a charge current associated with the first charge current rate.

In other embodiments, the first predetermined time period for the method is at least partially based on a threshold charge voltage. The meter can also have a liquid crystal display and the threshold charge voltage can be sufficient to conduct five or fewer blood glucose concentration tests. The first charge current rate and second charge current rate can also be generally constant.

In other embodiments, the method also includes notifying a user of the blood glucose meter with a perceivable signal following the first predetermined time period. A termination charge routine can also be implemented following the second predetermined time period that charges the battery at a third current rate until a predetermined event occurs, with the third charge current rate being lower than the second charge current rate. The third charge current rate can also be continuously decreasing.

In certain embodiments, a computer-readable medium is encoded with instructions for directing a rapid charge of a battery for a meter, such as a blood glucose meter. The meter will generally be conducting temperature-sensitive testing, such as determining an analyte concentration of a fluid sample. The instructions can include monitoring for a connection to an external power source. A rapid charge routine or algorithm can then be implemented for charging the battery at a first charge current until a first predetermined event occurs, such as the lapse of a certain time period or reaching a certain threshold voltage. Following the occurrence of the first predetermined event, a normal charge routine or algorithm can be implemented for charging the battery at a second charge current until a second predetermined event occurs. The first charge current is greater than the second charge current.

It is contemplated that certain embodiments of battery-powered meters, such as systems for testing blood glucose concentrations, can include a battery fuel gauge. For example, a battery fuel gauge integrated circuit can be incorporated into the system to determine the status of the charge for a battery. It is further contemplated that battery charge information can be used by a power management routine operating within the battery-powered meter system. The power management routine can allow the meter to operate over extended periods of time by managing power during periods of use and non-use. For example, a power management routine in a battery-powered blood glucose meter can allow for use of the meter over longer periods of time without having to recharge the battery by controlling power consumption during periods blood glucose concentration is analyzed and during periods between such analyses.

As described previously in the exemplary embodiment illustrated in FIG. 2, different types of rechargeable battery configurations may be used to power a meter including, lithium ion (Li-Ion), lithium polymer (Li—Po), nickel cadmium (NiCd), or nickel metal hydride (NiMH) batteries. The use of a lithium-based battery can provide certain benefits in the meter operation because the voltage across a lithium battery does not typically drop significantly during meter operation, that is, during the discharge process.

Figure 7:
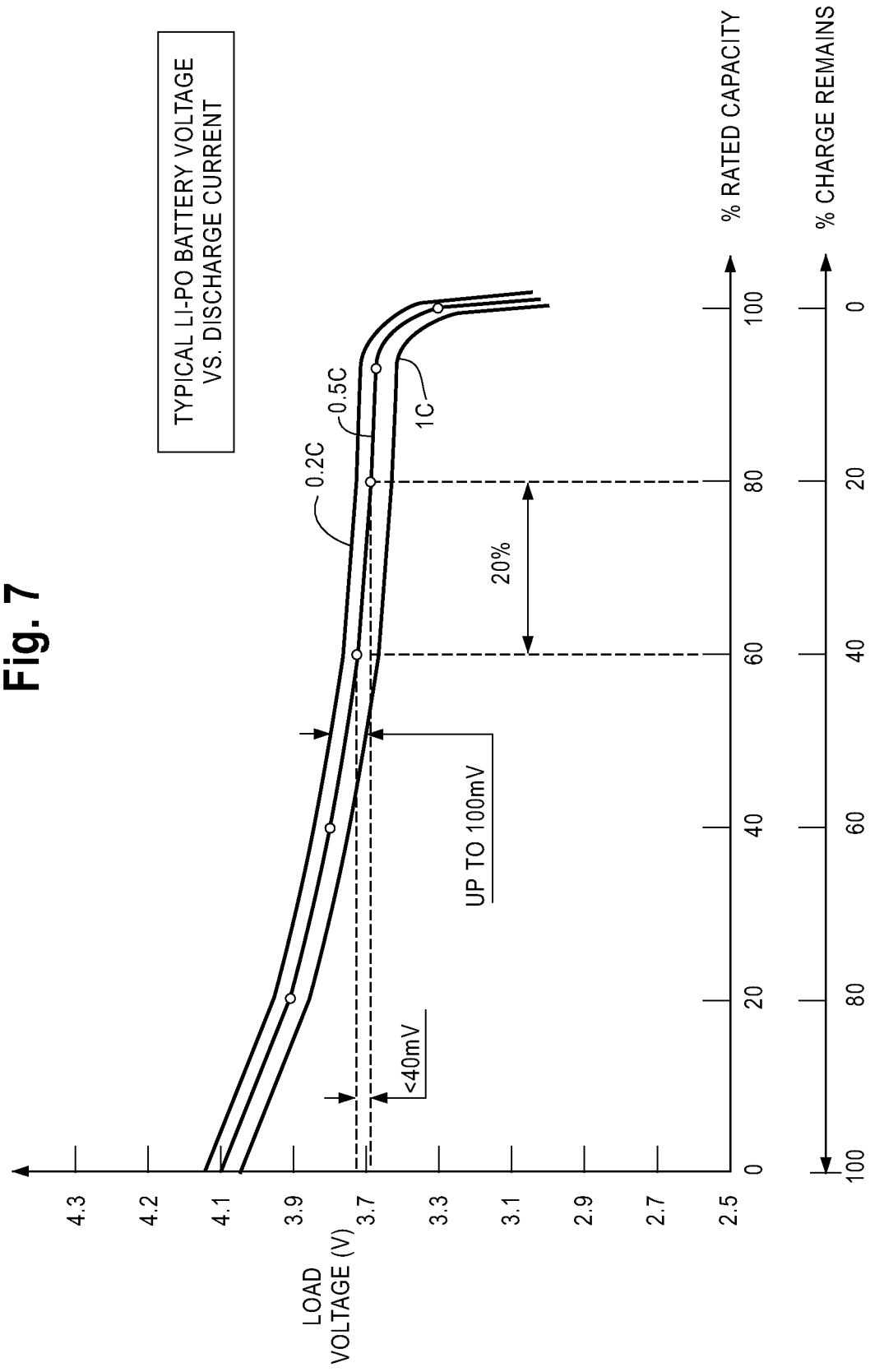
FIG. 7 illustrates a battery charge profile according to one embodiment.

FIG. 7 illustrates a battery discharge profile according to certain embodiments of the present application. The discharge profile illustrates the change in load voltage for a Li—Po battery during battery discharge during the operation of a meter, such as a blood glucose meter. The illustrated Li—Po battery has a fully-charged voltage of approximately 4.1 Volts. Discharge profiles are shown for the battery operating at 20, 50, and 100 percent of its rated capacity (C), that is, 0.2 C, 0.5 C, and 1 C, respectively. For example, with the Li—Po battery operating at 0.5 C, and over the range shifting from 40 percent of its remaining charge to 20 percent of its remaining charge, the Li—Po battery experiences a voltage change of approximately 40 millivolts or less. Even with fluctuations in the discharge current ranging from between 0.2 C and 1 C, voltage change in the illustrated Li—Po battery may span a 100 millivolt range. For an initial discharge current of 0.5 C, this may mean a voltage change of ±50 millivolts for shift in the discharge current down to 0.2 C, or up to 1 C. As further illustrated in FIG. 7, the load voltage for a Li—Po battery, such as one that may be used in a meter, can decrease significantly when less than five percent of the charge remains.

A battery fuel gauge can be beneficial for certain battery-powered devices—for example, portable meters using lithium batteries—because traditional direct voltage measurement methods that determine the state of battery charge do not typically work well for Li—Po or Li-Ion batteries. As illustrated, for example, in FIG. 7, the voltage across a lithium battery does not vary significantly during the discharging stage of the battery. To assess the remaining charge becomes difficult because of the small voltage changes in the lithium battery in which voltage changes can be attributed to the load placed on the battery by the battery-powered device or to the battery discharging. A battery fuel gauge can continuously monitor the current flowing through a battery in both directions—charging and discharging—counting, for example, the number of Coulombs the battery receives during charging and the number of Coulombs the battery loses during discharging.

Figure 8:
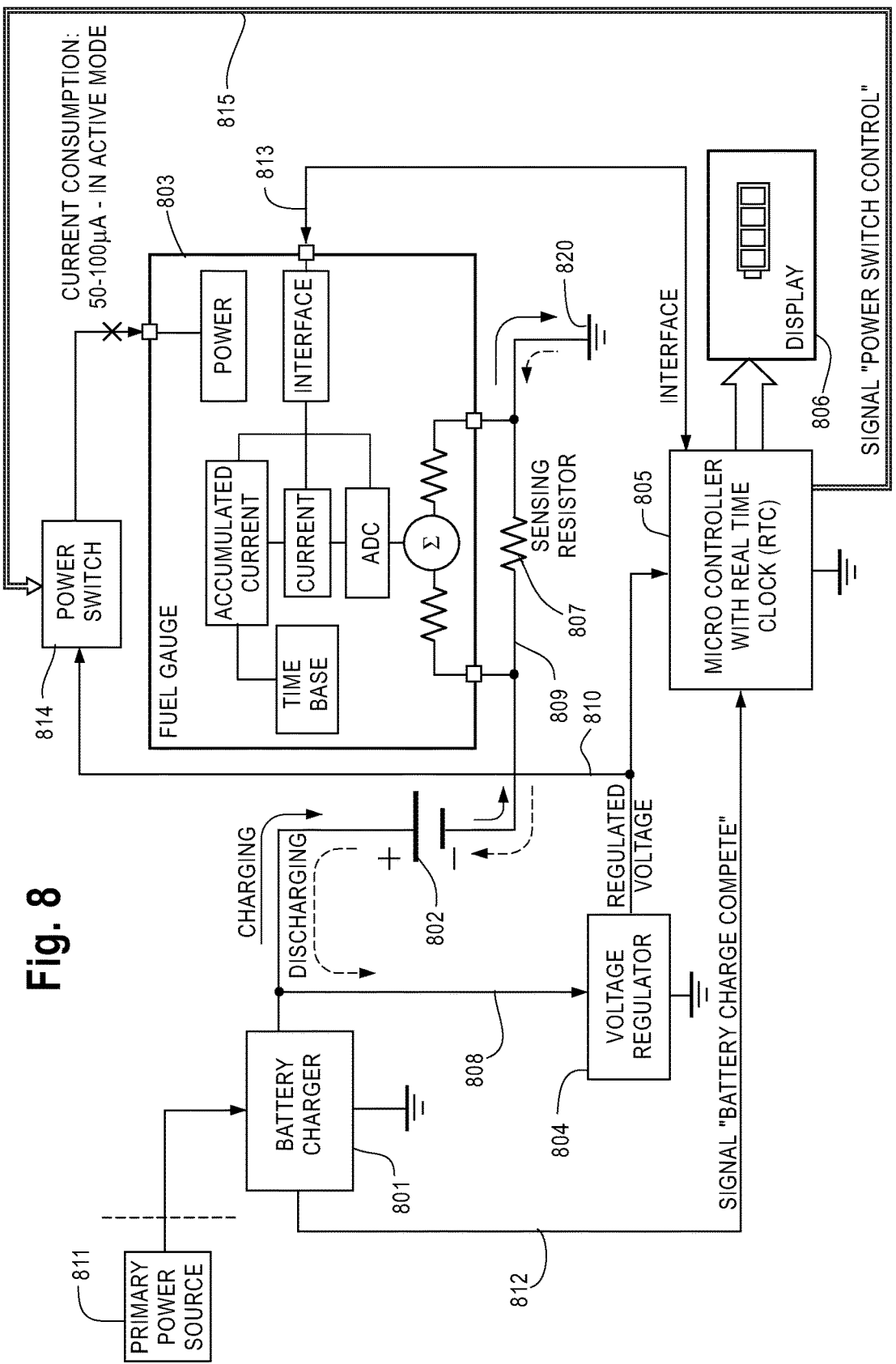
FIG. 8 illustrates a circuit for a meter with a fuel gauge and battery charger according to one embodiment.

FIG. 8 illustrates a circuit including a battery charger 801 with a fuel gauge 803 that can be applied to a meter, such as, for example, a blood glucose meter, according to certain embodiments of the present disclosure. The battery charger can be coupled with a primary power source 811. The primary power source may be a power outlet, a generator, an AC/DC wall-mount adapter, a USB port, or other power source capable of providing sufficient power to charge a battery. The battery charger 801 is connected to the positive electrode of a battery 802. The negative electrode of the battery 802 is coupled to ground 820 by way of a sensing resistor 807. As illustrated in FIG. 8, a microcontroller 805 and a fuel gauge 803 can be powered using a voltage regulator 804. The configuration of the voltage regulator 804 relative to the battery charger 801 and the battery 802 allows the voltage regulator to always receive power from either the battery charger 801—e.g., when the system is charging the battery—or the battery 802—e.g., when the system is discharging. An interface 813 between the microcontroller 805 and the fuel gauge 803 allows the transfer of information between the two devices so that the state of charge of the battery 802 can be determined. The microcontroller 805 can include a real-time clock and can further receive and process data from the fuel gauge 803. After the data from the fuel gauge is processed by the microcontroller 805, the microcontroller 805 can indicate the state of charge of the battery 802 on a display 806.

The embodiment illustrated in FIG. 8 allows a charging process in which current flows from the battery charger 801 to the battery 802. During the charging process, the current continues from the battery 802 to ground 820 by way of the sensing resistor 807. During the charging process, fuel gauge 803 monitors the voltage across sensing resistor 803 to determine the number of Coulombs that battery 802 receives from battery charger 801. When charging of the battery 802 is complete, the battery charger 801 sends a signal 812 to the microcontroller 805 that the battery charge is complete. The communication between the battery charger 812 and the microcontroller 805 that charging is complete further includes synchronizing the microcontroller 805 with the fuel gauge 803. Simultaneous or near simultaneous with the battery-charge-complete signal 812, the microcontroller can communicate with the display 806 so that a "Charge Complete" text, or an icon illustrating that the charge is complete, is shown in the display 806.

The battery charger 801 can be disconnected from the primary power source 811. When this occurs, the battery 802 then becomes the only source of power for the circuit illustrated in FIG. 8. Furthermore, upon the disconnection from the primary power source 811, the direction of current, previously flowing from the battery to the sensing resistor 807, changes or reverses. At this point, too, the fuel gauge 803 instantly or nearly instantly detects the reversed polarity of the voltage across the sensing resistor 807. The reversed polarity in the sensing resistor 807 triggers the fuel gauge 803 to start tracking the current out of the battery 802 by counting the energy units—that is, Coulombs—that leave the battery 802 as the battery is discharging. During the discharge phase of the circuit illustrated in FIG. 8, the microcontroller 805 and the fuel gauge 803 can communicate on a periodic, or near continuous basis, through interface 813 to allow the microcontroller to receive updates on the charge status of battery 802.

The primary power source 811 can be connected to the battery charger 801 at any time during the discharging process. The connection causes the current direction through the battery 802 to reverse and switch from a discharge mode to a charge mode. At or near the instant of the reversal of the current direction through the battery 802, the fuel gauge 803 tracks the current into the battery 802 by counting the number of Coulombs that enter the battery 802 during the charging process.

The charging and discharging processes can be regularly (e.g., periodic, continuous, etc.) monitored using the fuel gauge 803 and microcontroller 805. Through regular or continuous monitoring, the microcontroller 805 has updated information regarding the energy units remaining in the battery, which allows a relatively accurate assessment to be made of the state of battery charge in the battery 802. The state of the battery charge determined by the microcontroller 805 can then be shown on the display 806. The embodiment shown in display 806 is an icon with four bars to show the user the state of charge.

A feature that can be included within a portable or battery-powered meter is a sleep mode or stand-by mode, which limits the power consumption of a meter during periods of non-use or limited use. In the embodiment illustrated in FIG. 8, the microcontroller 805 can be used to place the circuit into a sleep mode. To limit the power consumption, it can be desirable for the fuel gauge 803 to be removed from the power distribution circuit when the microcontroller 805 places the system into a sleep mode. A power-switch-control signal 815 from the microcontroller 805 to a power switch 814, as illustrate in FIG. 8, can be used to isolate the fuel gauge 803.

The embodiment illustrated in FIG. 8 is beneficial because it allows the power consumption during a sleep mode to be reduced significantly. The energy use by a fuel gauge that continuously monitors the remaining battery charge can be significant. A continuously operating fuel gauge 803, even a low-power fuel gauge, can consume approximately 50-100 microamperes, even for a system placed into a sleep mode. Such power consumption in a portable battery-powered system, such as a blood glucose meter, can be considered significant. The microcontroller 805 may consume only a few microamperes (e.g., approximately 1-10 microamperes), even during a sleep mode.

In certain embodiments, the battery fuel gauge 803 is isolated and not allowed to consume power from a battery when a system is placed in a standby or sleep mode. A power switch 814 can be used to control the power directed by the voltage regulator 804 to the fuel gauge 803 during the discharging process—that is, when the primary power source 811 is disconnected. The voltage regulator 804 is placed within the circuit for to power the microcontroller 805 and fuel gauge 803 during the discharging process. The power switch 814 is connected to the microcontroller 805 so that the microcontroller can send a power-switch-control signal 815 to power switch 814. The power switch 814 will then either open or close the circuit that provides power to the fuel gauge 803. For example, if the microcontroller 805 determines that the meter should be entering into a standby or sleep mode, the microcontroller 805 sends a signal 815 to the power switch 814, which opens the circuit that directs current to the fuel gauge 803. In the illustration of FIG. 8, the opening of the circuit by way of power switch 814 removes a current consumption of approximately 50 to 100 microamperes from the battery 802. When the meter returns to an active mode, the microcontroller 805 can send another signal 815 to the power switch 814 to close the circuit between the battery 802 and the fuel gauge 803 so that the fuel gauge 803 can resume its function as current is reintroduced into the fuel gauge system 803.

It is desirable during the standby or sleep mode period for a meter to continue assessing the remaining life of a battery 802. For example, in the case of a blood glucose meter, a user may operate the device daily. It is also possible that the device may not be used, a thus, remain in a standby or sleep mode, for one or more days or for one or more weeks. In the embodiment illustrated in FIG. 8, the microcontroller 805 continues to draw a current of approximately 2 to 3 microamperes while in the sleep mode (e.g., very low power consumption). While the fuel gauge 803 can be removed from the power consumption circuit during the sleep mode, as illustrated in FIG. 8, it can be important to track the power consumption of the remaining power-drawing components, such as the microcontroller 805. But, the removal of the fuel gauge 803 from the power consumption circuit eliminates the fuel gauge 803 operation—that is the device that tracks current accumulation and consumption.

In certain embodiments, the assessment of remaining battery life or power consumption during the inactivity of a fuel gauge can be completed using a processor or microcontroller that includes a power management routine. A power management routine can extend the run time of a meter having a finite power source, such as, for example, a rechargeable battery.

In the embodiment of FIG. 8, the microcontroller 805 implementing a power management routine can perform several steps before entering into a standby or sleep mode. The microcontroller 805 includes a timer, or receives data from a timer. The timer maintains reference time(s) used in assessing the remaining charge in the battery 802. The timer may determine reference time(s) using a real-time clock. For example, before entering into a sleep mode, the microcontroller 805 records the reference time or an actual time along with recording the last state of the battery charge. The microcontroller 805 then sends a signal 815 to power switch 814 to open the circuit to fuel gauge 803—that is, remove the fuel gauge 803 from the power consumption loop. With the fuel gauge 803 not receiving power, consumption of power from the battery 802 is reduced significantly, but the fuel gauge stops tracking power consumption. However, prior to entering the sleep or standby mode, the recording of a reference time by the microcontroller 805 allows the determination of power consumption within the meter system after the microcontroller 805 wakes up. A meter may exit the sleep mode by a user prompting the meter. For example, the user may press a button or a predetermined wake-up criteria may be established for the meter.

After the microcontroller 805 receives a prompt to exit the standby or sleep mode, several operations occur to recalculate and restore the lost count of battery discharge during the inactivity of the fuel gauge 803. A power-switch-control signal 815 is sent to the power switch 814 to energize the battery fuel gauge 803. The microcontroller 805 also determines the duration of the standby or sleep mode by subtracting a first reference time that was recorded when the microcontroller 805 entered into the sleep mode currently being exited from a second reference time, e.g., the time at which the microcontroller wakes up or enters into an active mode. The microcontroller 805 then multiplies the calculated sleep mode duration by the known sleep mode current and voltage. The product of the sleep mode duration and the known current and voltage is the power consumed by the circuit during the standby or sleep mode. The microcontroller 805 then subtracts the calculated consumed power from the last recorded known state of battery charge—e.g., the remaining charge just before the last standby or sleep mode was entered. The result is an estimation of the state of the battery charge.

Figure 9:
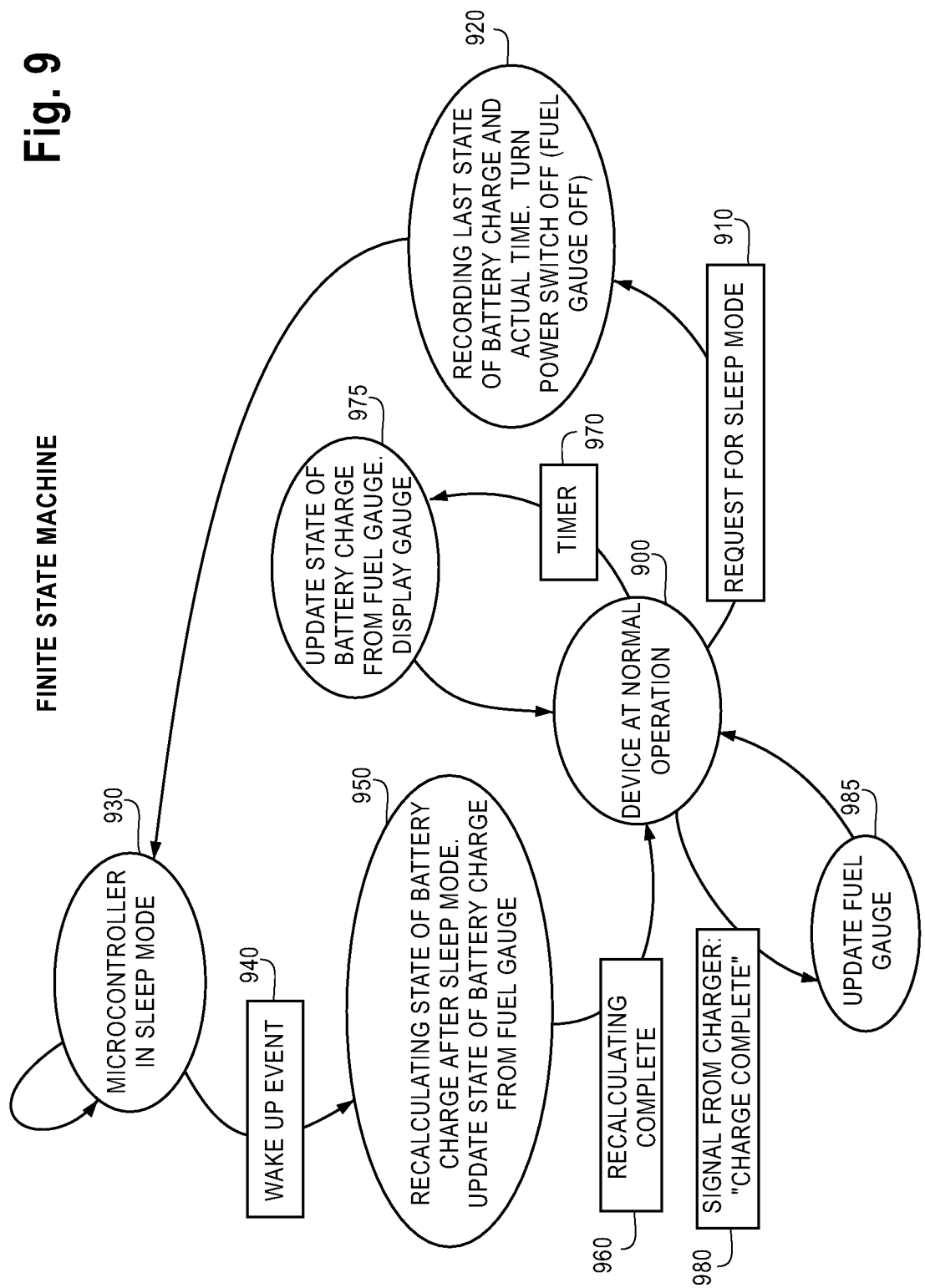
FIG. 9 illustrates a finite state machine of a power management method for a battery-powered device according to one embodiment.

FIG. 9 illustrates a finite state machine for a power management method for a battery-powered device according to certain embodiments of the present application. The power management method can be in the form of an algorithm or routine implemented on a computer or computerized system that monitors the power in a battery-powered device. For example, the method may be implemented in a system that includes a processor- or microcontroller-type device. The method can reduce the average power consumption of a fuel gauge integrated circuit while minimizing the loss of information about the exact state of battery charge.

In certain embodiments, a device, such as a meter—e.g., a battery-powered blood glucose meter—can be functioning in a normal operational state. The meter may be configured to operate in an active mode—e.g., normal mode—and a sleep mode—e.g., standby mode. Starting with the meter device at normal operation in step 900, a request to enter the sleep mode at step 910 can be received by a microcontroller. The request may occur based on input from a user or the lapse of a pre-determined period of time, which triggers the generation of a signal that is received by a processor or microcontroller. After the request for sleep mode at step 910 is received, the processor or microcontroller can record the time of the request and the state of battery charge at step 920 at the time of the request. In certain embodiments, the state of battery charge information will come from data received by the processor from a battery fuel gauge, such as the gauge illustrated in FIG. 8. To reduce power consumption during the sleep mode, a power switch controlling current to a fuel gauge can be opened to cut the power off to the fuel gauge. The microcontroller or processor can then keep the meter in a sleep mode at step 930 during which power consumption may be limited to the microcontroller. While in the sleep mode at step 930, the microcontroller can cycle and wait for the receipt of a signal identifying a wake-up event at step 940. The wake-up event at step 940 can include, for example, the receipt of an input from a user of the meter, the connection of a primary power source, a pre-selected triggering event, etc. After the wake-up event at step 940 is received by the microcontroller, the state of battery charge after the sleep mode is determined and the state of battery charge from the fuel gauge is updated at step 950. The update to the state of the battery charge can be determined using the sleep mode duration and the current and voltage that was in the circuit during the sleep mode. The wake up event at step 940 may also include sending a signal to a power switch that energizes the fuel gauge.

The state of battery charge after exiting the sleep mode can be determined immediately or shortly after the wake up event at step 940. After the updated state of the battery charge is determined at step 960, the meter can then reenter an mode of normal operation at step 900, e.g., an active mode. During the normal operation of a device at step 900, a timer at step 970, such as, for example, a real-time clock, can be used to allow reference times to be recorded, such as when a circuit changes between a charge mode, an active discharge mode, or a sleep discharge mode. During the normal operation mode, the state of battery charge can be continuously or periodically updated and illustrated on a display at step 975 using information received from the fuel gauge. During the normal operation of a device at step 900, such as a battery-powered blood glucose meter, a primary power source may be connected to a battery charger in the system. Monitoring of the battery charger can be completed until a signal is sent to the microcontroller that the charging is complete at step 980. At this point, another signal can be sent to update the fuel gauge at step 985 that the battery is completely charged. After the signal is sent to update the fuel gauge on the state of battery charge, the device can then cycle back to a normal operation mode at step 900.

In certain embodiments, a portable meter having a circuit is configured with a battery to provide power to a sensing element within the circuit. The meter includes a processor powered by the circuit. The processor is configured to operate the meter in an active mode and a sleep mode. A fuel gauge is powered by the circuit. The fuel gauge is configured to track state of battery charge data received from the battery during active mode operation of the meter. An interface is configured to transfer state of battery charge data from the fuel gauge to the processor. A power switch controls current flow to the fuel gauge and is configured to be open and closed by the processor. The processor signals the power switch into an open position if the meter enters into the sleep mode and the processor signals the power switch into a closed position if the meter enters into an active mode. Prior to entering the sleep mode, the processor is configured to record a first state of battery charge for the battery and a first time reference immediately prior to the meter entering said sleep mode. The processor is further configured to determine a second state of battery charge at a second reference time immediately after the meter exits from the sleep mode into the active mode. The second state of battery charge is determined based on the recorded first state of charge, the first reference time, the second reference time, and a pre-determined energy usage rate of the meter during the sleep mode.

In other embodiments, the portable meter is a blood glucose meter. The fuel gauge can continuously track the state of battery charge during the active mode of operation of the meter. The fuel gauge can be an integrated circuit. The portable meter can further include a display coupled to the processor in which the display is configured to display the present state of battery charge. The processor can be a microcontroller. The battery can be a rechargeable battery. The portable meter can enter into the active mode when a primary power source is charging the battery.

According to another embodiment, a method of power management includes a battery-powered meter that is configured to operate in an active mode and a standby mode. The batter-powered meter includes a battery fuel gauge and a microcontroller. The method includes the steps of receiving a first request to enter into the standby mode. A first state of charge is recorded for a battery of the meter. The recording occurs at a first reference time immediately after the first request is received. The first reference time is recorded using the microcontroller. The meter is entered into the standby mode with the power to the battery fuel gauge being switched off in the standby mode. A second request to exit the standby mode and enter the active mode is received at a second reference time. The second reference time occurs after the first reference time. In response to the second request, a second reference time is immediately recorded and the microcontroller determines a second state of battery charge based on the first reference time, the second reference time, a standby mode current, and a standby mode voltage of the meter.

In other embodiments, the first state of battery charge for the battery is determined using the battery fuel gauge. The battery-powered meter can be initially operating in an active mode. If the meter is in an active mode, a state of battery charge can be updated using battery charge data received by the microcontroller from the battery fuel gauge. Updating can be continuous. The state of battery charge can be displayed on a display gauge.

According to a further embodiment, a computer-readable memory medium has stored thereon instructions for managing the power of a battery-powered meter operating in an active mode and a sleep mode. The instructions includes the steps of receiving a first request to enter into the sleep mode and recording a first state of charge for a battery of the meter. The recording occurs at a first reference time immediately after the first request is received. A first reference time is recorded. The meter is entered into the standby mode wherein power to a battery fuel gauge is switched off in the standby mode. A second request is received at a second reference time to exit the sleep mode and enter the active mode. The second reference time occurs after the first reference time. Immediately after the second request, a second reference time is recorded. A second state of battery charge is determined based on the first reference time, the second reference time, a sleep mode current, and a sleep mode voltage.

In certain embodiments, a meter may incorporate multiple operations, such as, for example, a blood glucose concentration testing operation and global positioning systems. Such multiple operations on a portable meter may require additional power from a battery. The power requirements can be supplied using a larger battery, efficient power management techniques, or a combination of both.

While the invention has been described with reference to details of the illustrated embodiments, these details are not intended to limit the scope of the invention as defined in the appended claims. For example, the rapid charge system for the battery may be used in various heat-sensitive applications. The disclosed embodiments and obvious variations thereof are contemplated as falling within the spirit and scope of the claimed invention.

What is claimed is:

1. A blood-glucose meter including a circuit configured with a rechargeable battery to provide power to a sensing element for determining a blood-glucose concentration of a fluid sample, the blood-glucose meter comprising:
    a housing defining a port sized to receive at least a portion of a test sensor, the rechargeable battery and the circuit being at least partially disposed within the housing;
    a processor powered by the circuit and disposed within the housing, the processor configured to operate the meter in an active mode and a sleep mode;
    a fuel gauge powered by the circuit, the fuel gauge disposed within the housing and configured to track state of battery charge data received from the battery during the active mode of operation of the meter;
    an interface configured to transfer state of battery charge data from the fuel gauge to the processor; and
    a switch for controlling current flow to the fuel gauge, the switch configured to be open and closed by the processor, the processor signaling the switch to an open position to disconnect the fuel gauge from the circuit if the meter enters into the sleep mode and the processor signaling the switch to a closed position if the meter enters into the active mode.

2. The blood-glucose meter of claim 1, wherein the processor is configured to determine a state of battery charge after the blood glucose meter enters into the active mode.

3. The blood-glucose meter of claim 1, wherein the fuel gauge continuously tracks state of battery charge during the active mode of operation of the blood-glucose meter.

4. The blood-glucose meter of claim 1, wherein the processor is configured to determine updated states of battery charge during the active mode of operation using battery charge data received from the battery fuel gauge.

5. The blood-glucose meter of claim 4, wherein the determining of updated states of battery charge is continuous.

6. The blood-glucose meter of claim 1, wherein the fuel gauge is an integrated circuit.

7. The blood-glucose meter of claim 1, further comprising a display coupled to the processor, the display configured to display a present state of battery charge.

8. The blood-glucose meter of claim 1, wherein the processor is a microcontroller.

9. The blood-glucose meter of claim 1, wherein the blood-glucose meter enters into the active mode when a primary power source is charging the battery.

10. A non-transitory computer-readable medium disposed within a housing of a blood-glucose meter configured to operate in an active mode and a standby mode, the housing including a port configured to receive a test sensor, the blood-glucose meter including a battery fuel gauge powered by a power distribution circuit, the computer-readable memory medium having stored thereon an instruction set for managing the power of the blood-glucose meter, the instruction set being configured to implement, upon execution by a processor disposed within the housing, acts comprising:
    receiving a first input to enter a standby mode;
    entering the blood-glucose meter into the standby mode, wherein power to the battery fuel gauge is switched off in the standby mode thereby disconnecting the battery fuel gauge from the power distribution circuit;
    receiving a subsequent input to exit the standby mode and enter the active mode, wherein power to the battery fuel gauge is switched on in the active mode; and
    determining a state of battery charge after the meter enters into the active mode.

11. The non-transitory computer-readable medium of claim 10, wherein said instruction set is further configured to implement, upon execution by the processor, the act comprising updating a state of battery charge using battery charge data received by the processor from the battery fuel gauge if the meter is in the active mode.

12. The non-transitory computer-readable medium of claim 11, wherein the updating is continuous.

13. The non-transitory computer-readable medium of claim 10, wherein the fuel gauge is an integrated circuit.

14. The non-transitory computer-readable medium of claim 10, wherein said instruction set is further configured to implement, upon execution by the processor, the act comprising displaying a present state of battery charge on a display.

15. The non-transitory computer-readable medium of claim 10, wherein the processor is a microcontroller.

16. The non-transitory computer-readable medium of claim 10, wherein the blood-glucose meter enters into the active mode when a primary power source is charging the battery.

* * * * *